US008219192B2

(12) United States Patent
Shuros et al.

(10) Patent No.: US 8,219,192 B2
(45) **Date of Patent: *Jul. 10, 2012**

(54) METHOD AND APPARATUS FOR TRANSCUTANEOUS CARDIOPROTECTIVE PACING

(75) Inventors: Allan C. Shuros, St. Paul, MN (US); Eric A. Mokelke, White Bear Lake, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 438 days.

This patent is subject to a terminal disclaimer.

(21) Appl. No.: 12/496,504

(22) Filed: Jul. 1, 2009

(65) Prior Publication Data

US 2010/0010551 A1 Jan. 14, 2010

Related U.S. Application Data

(60) Provisional application No. 61/079,008, filed on Jul. 8, 2008.

(51) Int. Cl.
*A61N 1/00* (2006.01)

(52) U.S. Cl. .......... 607/4

(58) Field of Classification Search .......... 607/4, 10, 607/11, 2, 50, 63, 9
See application file for complete search history.

(56) References Cited

U.S. PATENT DOCUMENTS 5,078,134 A 1/1992 Heilman et al.
5,193,537 A 3/1993 Freeman
5,205,284 A 4/1993 Freeman
5,282,843 A 2/1994 Freeman
5,284,135 A 2/1994 Lopin
5,431,688 A * 7/1995 Freeman .......... 607/10
5,782,882 A 7/1998 Lerman et al.
5,891,045 A 4/1999 Albrecht et al.
6,526,303 B1 2/2003 Scampini
6,711,442 B1 3/2004 Swerdlow et al.
6,772,008 B2 8/2004 Zhu et al.
2003/0069510 A1 4/2003 Semier
2004/0138713 A1 7/2004 Stickney et al.
2004/0215258 A1* 10/2004 Lovett et al. .......... 607/9
2006/0241704 A1 10/2006 Shuros et al.
2008/0065160 A1 3/2008 Brink
2009/0076561 A1* 3/2009 Libbus et al. .......... 607/11
2010/0249860 A1 9/2010 Shuros et al.

FOREIGN PATENT DOCUMENTS

WO WO-2005/118063 A1 12/2005

(Continued)

OTHER PUBLICATIONS

"International Application Serial No. PCT/US2010/026640, International Search Report mailed May 7, 2010", 5 pgs.

(Continued)

*Primary Examiner* — George Manuel
*Assistant Examiner* — Robert Wieland
(74) *Attorney, Agent, or Firm* — Schwegman, Lundberg & Woessner, P.A.

(57) ABSTRACT

A transcutaneous cardiac stimulation system delivers pacing pulses according to a cardioprotective pacing protocol. The pacing pulses are delivered through body-surface electrodes attached onto a patient. The cardioprotective pacing protocol specifies pacing parameters selected to augment cardiac stress on the patient's myocardium to a level effecting cardioprotection against ischemic and reperfusion injuries.

24 Claims, 6 Drawing Sheets

100
102
101
105H
106H
105A
105B
105C
105D
105E
105F
105G
106A
106B
106C
106D
106E
106F
106G
120
108
122
121
124
126
125
110
112

FOREIGN PATENT DOCUMENTS

WO WO-2008/120154 A2 10/2008
WO WO-2010111028 A1 9/2010

OTHER PUBLICATIONS

"International Application Serial No. PCT/US2010/026640, Written Opinion mailed May 7, 2010", 8 pgs.
Azevedo, J. G., et al., "O pacemaker transcutaneo ern emergencies cardiovasculares [Transcutaneous pacemaker in cardiovascular emergencies]", *Rev. Port. Cardiol.*, 10(9), (w/ English Abstract), (1991), 665-668.
Bocka, J. J, "External Transcutaneous Pacemakers", *Ann Emerg Med.*, 18(12), (Dec. 1989), 1280-1286.
Gammage, M. D., "Temporary cardiac pacing", *Heart*, 83(6), (Jun. 2000), 715-720.
Zoll, P. M, et al., "External noninvasive temporary cardiac pacing: clinical trials", *Circulation*, 71(5), (May, 1985), 937-944.
"International Application Serial No. PCT/US2010/026640, Preliminary Report on Patentability mailed Oct. 6, 2011", 9 pgs.

* cited by examiner

METHOD AND APPARATUS FOR TRANSCUTANEOUS CARDIOPROTECTIVE PACING

CROSS-REFERENCE TO RELATED APPLICATION

This application claims the benefit of U.S. Provisional Application No. 61/079,008, filed on Jul. 8, 2008, under 35 U.S.C. §119(e), which is hereby incorporated by reference.

TECHNICAL FIELD

This document relates generally to cardiac stimulation systems and particularly to a transcutaneous cardiac stimulation system delivering cardioprotective pacing.

BACKGROUND

The heart is the center of a person's circulatory system. It includes an electro-mechanical system performing two major pumping functions. The left portions of the heart draw oxygenated blood from the lungs and pump it to the organs of the body to provide the organs with their metabolic needs for oxygen. The right portions of the heart draw deoxygenated blood from the body organs and pump it to the lungs where the blood gets oxygenated. These pumping functions are resulted from contractions of the myocardium (cardiac muscles). In a normal heart, the sinoatrial node, the heart's natural pacemaker, generates electrical impulses, called action potentials, that propagate through an electrical conduction system to various regions of the heart to excite the myocardial tissues of these regions. Coordinated delays in the propagations of the action potentials in a normal electrical conduction system cause the various portions of the heart to contract in synchrony to result in efficient pumping functions. A blocked or otherwise abnormal electrical conduction and/or deteriorated myocardial tissue cause dyssynchronous contraction of the heart, resulting in poor hemodynamic performance including a diminished blood supply to the heart and the rest of the body. The condition in which the heart fails to pump enough blood to meet the body's metabolic needs is known as heart failure.

Myocardial infarction (MI) is the necrosis of portions of the myocardial tissue resulted from cardiac ischemia, a condition in which the myocardium is deprived of adequate oxygen supply and metabolite removal due to an interruption in blood supply caused by an occlusion of a blood vessel such as a coronary artery. The necrotic tissue, known as infarcted tissue, loses the contractile properties of the normal, healthy myocardial tissue. Consequently, the overall contractility of the myocardium is weakened, resulting in an impaired hemodynamic performance. Following an MI, cardiac remodeling starts with expansion of the region of infarcted tissue and progresses to a chronic, global expansion in the size and change in the shape of the entire left ventricle. The consequences include a further impaired hemodynamic performance and a significantly increased risk of developing heart failure.

When a blood vessel such as the coronary artery is partially or completely occluded, a revascularization procedure such as pharmacological reperfusion or mechanical reperfusion (percutaneous coronary intervention) can be performed to reopen the occluded blood vessel. In addition to the ischemic injury resulting from MI and percutaneous coronary intervention, reperfusion that follows the reopening of the occluded blood vessel is also known to cause cardiac injury, known as reperfusion injury. In addition, plaques dislodged and displaced by the revascularization procedure may enter small blood vessels branching from the blood vessel in which the revascularization is performed, causing occlusion of these small blood vessels. The revascularization procedure may also cause distal embolization, i.e., obstruction of the artery caused by the plaque dislodged during the procedure. Therefore, there is a need for minimizing cardiac injury associated with ischemia and reperfusion.

SUMMARY

A transcutaneous cardiac stimulation system delivers pacing pulses according to a cardioprotective pacing protocol. The pacing pulses are delivered through body-surface electrodes attached onto a patient. The cardioprotective pacing protocol specifies pacing parameters selected to augment cardiac stress on the patient's myocardium to a level effecting cardioprotection against ischemic and reperfusion injuries.

In one embodiment, the transcutaneous cardiac stimulation includes a transcutaneous cardiac stimulation device and the body-surface electrodes. The transcutaneous cardiac stimulation device includes a pacing output circuit and a pacing control circuit. The pacing output circuit produces pacing pulses suitable for capturing the heart by transcutaneous delivery. The pacing control circuit controls the transcutaneous delivery of the pacing pulses by executing a pacing protocol and includes a pacing protocol module to store the pacing protocol. The pacing protocol includes the cardioprotective pacing protocol. The body-surface electrodes include a pacing electrode set electrically wired to the pacing output circuit. The pacing electrode set includes at least two electrodes through which the pacing pulses are transcutaneously delivered to the patient's heart.

In one embodiment, a non-invasive cardioprotective pacing method is provided. Pacing pulses are transcutaneously to the heart through a pacing electrode set including two or more electrodes selected from a plurality of body-surface electrodes attached onto the patient's body. The delivery of the pacing pulses is controlled by executing the cardioprotective pacing protocol.

This Summary is an overview of some of the teachings of the present application and not intended to be an exclusive or exhaustive treatment of the present subject matter. Further details about the present subject matter are found in the detailed description and appended claims. Other aspects of the invention will be apparent to persons skilled in the art upon reading and understanding the following detailed description and viewing the drawings that form a part thereof. The scope of the present invention is defined by the appended claims and their legal equivalents.

BRIEF DESCRIPTION OF THE DRAWINGS

The drawings illustrate generally, by way of example, various embodiments discussed in the present document. The drawings are for illustrative purposes only and may not be to scale.

DETAILED DESCRIPTION

In the following detailed description, reference is made to the accompanying drawings which form a part hereof, and in which is shown by way of illustration specific embodiments in which the invention may be practiced. These embodiments are described in sufficient detail to enable those skilled in the art to practice the invention, and it is to be understood that the embodiments may be combined, or that other embodiments may be utilized and that structural, logical and electrical changes may be made without departing from the spirit and scope of the present invention. The following detailed description provides examples, and the scope of the present invention is defined by the appended claims and their legal equivalents.

It should be noted that references to "an", "one", or "various" embodiments in this disclosure are not necessarily to the same embodiment, and such references contemplate more than one embodiment.

This document discusses, among other things, a transcutaneous cardiac stimulation system that delivers pacing pulses using body-surface electrodes attached onto a patient whose myocardium suffers ischemic injury from cardiac ischemia or MI. When available and appropriate, a revascularization procedure using pharmacological or mechanical means is performed to reopen the completely or partially occluded blood vessel associated with the ischemia or MI. An example of the pharmacological means is intravenous administration of tissue plasminogen activator (tPA), which dissolves the plaque that occludes the blood vessel. An example of the mechanical means is a percutaneous transluminal vascular intervention (PTVI) procedure, such as a percutaneous transluminal coronary angioplasty (PTCA) procedure. Such revascularization may cause reperfusion injury when the blood vessel is reopened. The transcutaneous cardiac stimulation system delivers an acute pacing cardioprotection therapy to the patient according to a cardioprotective pacing protocol that specifies a pacing sequence for augmenting the patient's cardiac stress to a level effecting cardioprotection against the ischemic and reperfusion injuries. The system allows the acute pacing cardioprotection therapy to be delivered promptly and non-invasively in response to a detection of the cardiac ischemia or MI, before, during, and/or after the revascularization procedure.

Figure 1:
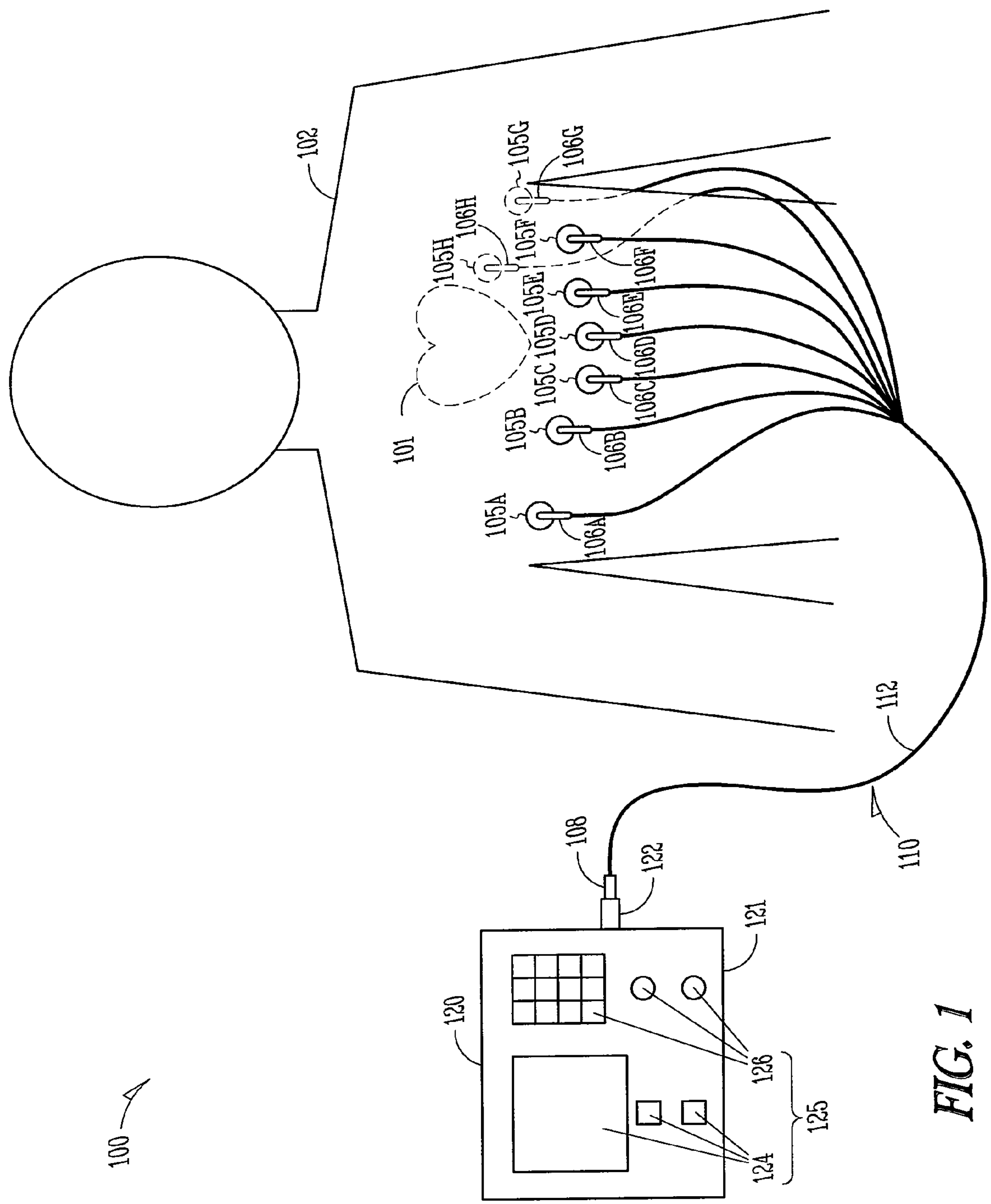
FIG. 1 is an illustration of an embodiment of a transcutaneous cardiac stimulation system providing for cardioprotective pacing, including a transcutaneous cardiac stimulation and a plurality of body-surface electrodes, and portions of an environment in which the system is used.

FIG. 1 is an illustration of an embodiment of a transcutaneous cardiac stimulation system 100 providing for cardioprotective pacing and portions of an environment in which system 100 is used. System 100 is an external, non-invasive system that includes a transcutaneous cardiac stimulation device 120, a plurality of body-surface electrodes 105A-H, and a cable 110 providing for electrical connection between device 120 and electrodes 105A-H.

Transcutaneous cardiac stimulation device 120 includes a chassis 121 housing circuitry for delivering the pacing cardioprotection therapy that protects the heart from the ischemic and reperfusion injuries. A user interface 125, including presentation devices 124 and user input devices 126, is incorporated onto chassis 121 to allow a user to control the delivery of the pacing cardioprotection therapy. Pacing pulses are delivered according to the cardioprotective pacing protocol to a heart 101 of the patient's body 102 through a pacing electrode set selected from a plurality of body-surface electrodes 105A-H. The pacing electrode set includes two or more electrodes. In one embodiment, transthoracic pacing is delivered using two electrodes placed on body 102 with heart 101 in the path of pacing current, such as electrodes 105H and 105C.

Body-surface electrodes 105A-H are attached onto the skin of body 102. In one embodiment, body-surface electrodes 105A-H are each an adhesive pad electrode. Cable 110 includes a proximal connector 108, a plurality of distal connectors 106A-H, and an elongate cable body 112 connecting between connector(s) 108 and connectors 106A-H. Proximal connector 108 is configured to mate a cable connector 122 mounted on chassis 121 of transcutaneous cardiac stimulation device 120. Cable connector 122 provides for an interface between the circuitry of transcutaneous cardiac stimulation device 120 and electrodes 105A-H. Distal connectors 106A-H are each configured to be connected to one of electrodes 105A-H. Electrodes 105A-H and cable 110 are illustrated in FIG. 1 by way of example.

In various embodiments, transcutaneous cardiac stimulation device 120 delivers pacing cardioprotection therapies including pacing pre-conditioning (cardioprotective pacing before the onset of an anticipated ischemic or reperfusion event) and pacing post-conditioning (cardioprotective pacing after the onset of the ischemic or reperfusion event). In one embodiment, transcutaneous cardiac stimulation device 120 also delivers defibrillation pulses through a defibrillation electrode set including two or more electrodes selected from body-surface electrodes 105A-H. In one embodiment, transcutaneous cardiac stimulation device 120 includes an automatic external defibrillator (AED) with pacing capability. Thus, system 100 is capable of providing for non-invasive, transthoracic, and transcutaneous delivery of pacing cardioprotection and defibrillation therapies.

In various embodiments, system 100 includes any number and configuration of body-surface electrodes suitable for delivering the pacing pulses and performing other functions discussed in this document. Cable 110 has various configurations capable of providing electrical connections between the circuitry of transcutaneous cardiac stimulation device 120 and the body-surface electrodes.

In one embodiment, system 100 is used to deliver the pacing cardioprotection therapy when a percutaneous or implantable stimulation system is not timely available or not suitable for the patient. For example, if prompt delivery of the pacing cardioprotection therapy is beneficial to the patient, system 100 is used when the patient is in an ambulance, or in an emergency room or catheterization laboratory waiting for a revascularization procedure.

In various embodiments, the circuit of transcutaneous cardiac stimulation device 120, including its various elements discussed in this document, is implemented using a combination of hardware and software. In various embodiments, each element of transcutaneous cardiac stimulation device

120 discussed in this document may be implemented using an application-specific circuit constructed to perform one or more particular functions or a general-purpose circuit programmed to perform such function(s). Such a general-purpose circuit includes, but is not limited to, a microprocessor or a portion thereof, a microcontroller or portions thereof, and a programmable logic circuit or a portion thereof.

Figure 2:
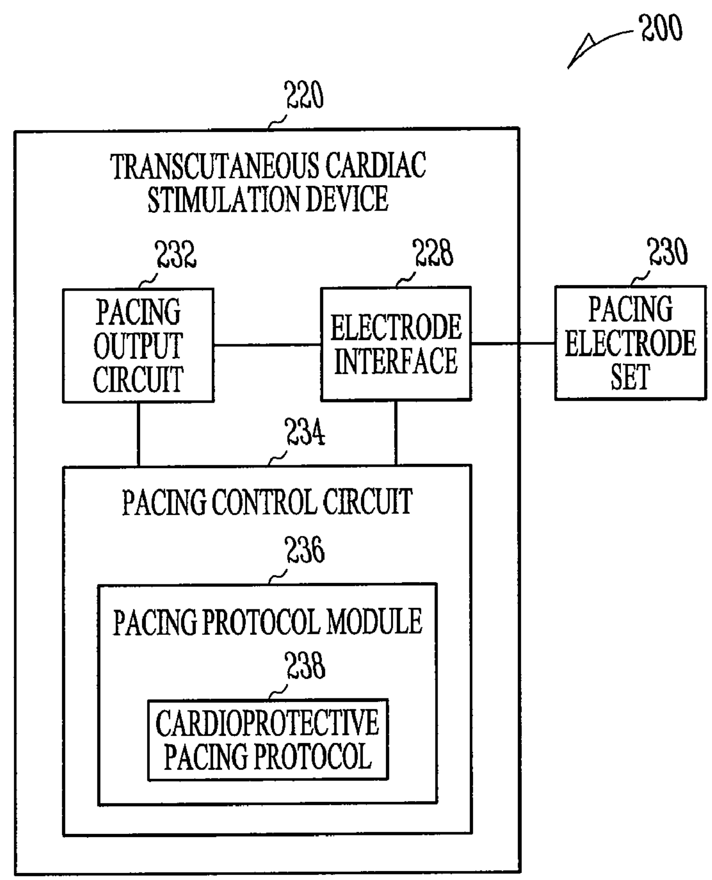
FIG. 2 is a block diagram illustrating an embodiment of the transcutaneous cardiac stimulation system.

FIG. 2 is a block diagram illustrating an embodiment of a transcutaneous cardiac stimulation system 200, which includes a transcutaneous cardiac stimulation device 220 electrically coupled to a pacing electrode set 230. Transcutaneous cardiac stimulation device 220 is an embodiment of transcutaneous cardiac stimulation device 120 and includes a pacing output circuit 232, a pacing control circuit 234, and an electrode interface 228. Pacing output circuit 232 produces pacing pulses suitable for capturing heart 101 by transcutaneous delivery through pacing electrode set 230. Pacing control circuit 234 controls the transcutaneous delivery of the pacing pulses by executing a pacing protocol and includes a pacing protocol module 236. Pacing protocol module 236 stores one or more pacing protocols including a cardioprotective pacing protocol 238. Cardioprotective pacing protocol 238 specifies a pacing sequence timing delivery of pacing pulses to augment mechanical stress on the myocardium of heart 101 to a level effecting cardioprotection against myocardial injury. Electrode interface 228 provides for the electrical connections between pacing output circuit 232 and pacing electrode set 230. Pacing electrode set 230 includes two or more electrodes attached onto body 102. In one embodiment, pacing electrode set 230 includes two or more electrodes selected from a plurality of body-surface electrodes such as electrodes 105A-H. In one embodiment, the selection of pacing electrode set 230 from the plurality of body-surface electrodes is adjustable by programming electrode interface 228.

Figure 3:
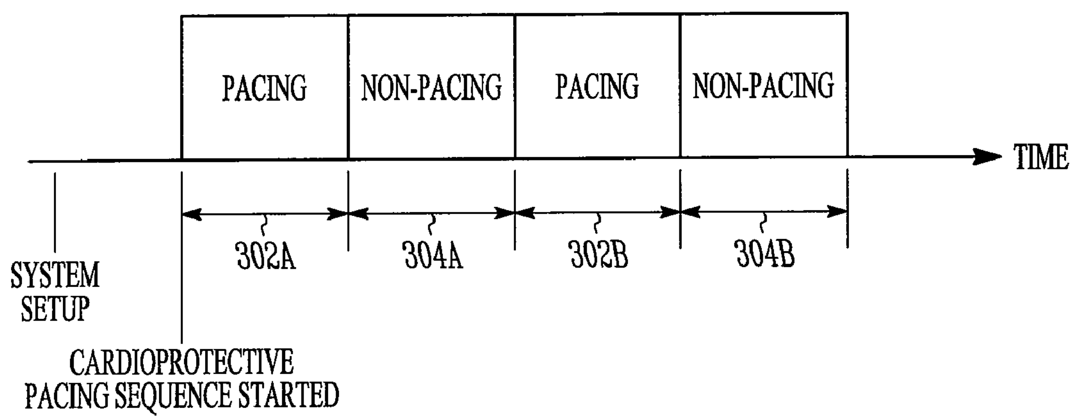
FIG. 3 is a timing diagram illustrating an embodiment of a cardioprotective pacing protocol.

FIG. 3 is a timing diagram illustrating an embodiment of a cardioprotective pacing protocol being an example of cardioprotective pacing protocol 238. The cardioprotective pacing protocol specifies a cardioprotective pacing sequence. The cardioprotective pacing sequence is started after a pacing system such as system 100 is set up as illustrated in FIG. 1. In various embodiments, the cardioprotective pacing sequence is started before, during, and/or after an ischemic or reperfusion event.

As illustrated in FIG. 3, the cardioprotective pacing sequence includes alternating pacing and non-pacing periods. Each pacing period is a pacing duration during which the pacing pulses are delivered in a specified pacing mode. Each non-pacing period is a non-pacing duration during which no pacing pulse is delivered. FIG. 3 shows, by way of example, a cardioprotective pacing sequence that includes two cycles of alternating pacing and non-pacing periods: pacing period 302A, non-pacing periods 304A, pacing period 302B, and non-pacing periods 304B. In one embodiment, the number of the cycles of alternating pacing and non-pacing periods is programmable, and each of the pacing and non-pacing periods is programmable. In one embodiment, the cardioprotective pacing sequence is initiated before the ischemic or reperfusion event and includes approximately 1 to 10 cycles of alternating pacing and non-pacing periods. The pacing period is in a range of approximately 15 seconds to 20 minutes. The non-pacing period is in a range of approximately 5 seconds to 20 minutes. In a specific example, the cardioprotective pacing sequence initiated before the ischemic or reperfusion event includes 3 cycles of alternating pacing and non-pacing periods each being approximately 5-minute long. In one embodiment, the cardioprotective pacing sequence is initiated during the ischemic or reperfusion event and includes approximately 1 to 10 cycles of alternating pacing and non-pacing periods. The pacing period is in a range of approximately 15 seconds to 20 minutes. The non-pacing period is in a range of approximately 5 seconds to 20 minutes. In a specific example, the cardioprotective pacing sequence delivered during the ischemic or reperfusion event includes 3 cycles of alternating pacing and non-pacing periods each being approximately 5-minute long. In one embodiment, the cardioprotective pacing sequence is initiated after the ischemic or reperfusion event and includes approximately 1 to 10 cycles of alternating pacing and non-pacing periods. The pacing period is in a range of approximately 10 seconds to one minute. The non-pacing period is in a range of approximately 5 seconds to one minute. In one specific example, the cardioprotective pacing sequence delivered after the ischemic or reperfusion event includes 2 to 4 cycles of alternating pacing and non-pacing periods each being approximately 30-second long.

The specified pacing mode is selected to augment the mechanical stress on the patient's myocardium to a level effecting cardioprotection against myocardial injury by delivering the pacing pulses. In one embodiment, during each pacing period, rapid, asynchronous pacing is applied. In other words, pacing pulses are delivered at a rate substantially higher than the patient's intrinsic heart rate without being synchronized to the patient's intrinsic cardiac contractions. In various other embodiments, the cardioprotective pacing sequence includes pacing at one or more atrial tracking or other pacing modes. Examples of pacing modes used in such a cardioprotective pacing sequence include VDD, VVI, and DDD modes. In various embodiments, the VVI and DDD modes are delivered with a lower rate limit higher than the patient's intrinsic heart rate, such as by 10-20 beats per minute.

Figure 4:
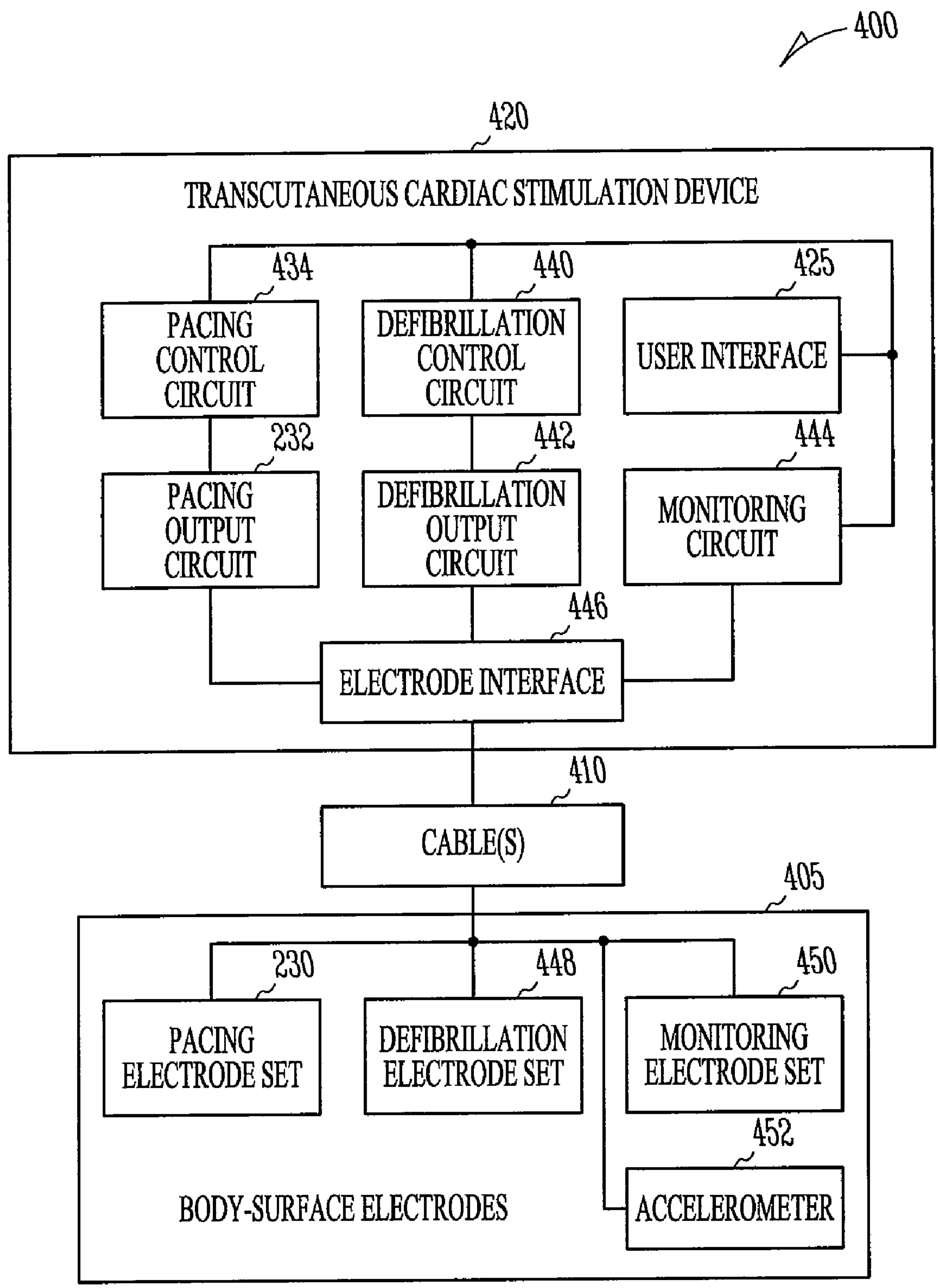
FIG. 4 is a block diagram illustrating another embodiment of the transcutaneous cardiac stimulation system.

FIG. 4 is a block diagram illustrating an embodiment of a transcutaneous cardiac stimulation system 400, which is another embodiment of transcutaneous cardiac stimulation system 100. System 400 includes a transcutaneous cardiac stimulation device 420, body-surface electrodes 405, and a cable 410 connecting device 420 and electrodes 405.

Transcutaneous cardiac stimulation device 420 is an embodiment of transcutaneous cardiac stimulation device 220 and includes pacing output circuit 232, a defibrillation output circuit 442, a monitoring circuit 444, a pacing control circuit 434, a defibrillation control circuit 440, a user interface 425, and an electrode interface 446. Defibrillation output circuit 442 delivers defibrillation pulses suitable for defibrillating the heart by transcutaneous delivery. Monitoring circuit 444 monitors the patient's conditions related to the delivery of the pacing pulses and defibrillation pulses. Pacing control circuit 434 performs the functions of pacing control circuit 234 and in addition, controls the delivery of the pacing pulses using the patient's conditions monitored by monitoring circuit 444 and coordinates the delivery of the pacing pulses with the delivery of the defibrillation pulses. Defibrillation control circuit 440 controls the delivery of the defibrillation pulses. In one embodiment, defibrillation control circuit 440 initiates the delivery of a defibrillation pulse in response to one of a defibrillation command received by user interface 425 and a tachyarrhythmia detection signal indicative of the detection of a tachyarrhythmia episode by monitoring circuit 444. The tachyarrhythmia episode to be detected includes one or more specified types indicated for a defibrillation therapy. Electrode interface 446 includes one or more cable connectors such as cable connector(s) 122. In one embodiment, electrode interface 446 includes programmable connections between transcutaneous cardiac stimulation device 420 and body-surface electrodes 405 via cable 410 for routing the pacing pulses, defibrillation pulses, and signals indicative the patient's conditions being monitored. User interface 425 is an embodiment of user interface 125 and receives user commands for controlling the delivery of pacing and defibrillation pulses and presents various signals indicative of the patient's conditions and/or operational status of transcutaneous cardiac stimulation device 420.

Body-surface electrodes 405 are configured for skin attachment and include a pacing electrode set 230, a defibrillation electrode set 448, a monitoring electrode set 450, and an accelerometer 452. In one embodiment, body-surface electrodes 405 each include an adhesive pad configured to be attached onto the skin. One example of body-surface electrodes 405 includes electrodes 105A-H. Defibrillation output circuit 442 delivers the defibrillation pulses transcutaneously through defibrillation electrode set 448, which includes two or more electrodes selected from body-surface electrodes 405. In one embodiment, monitoring electrode set 450 includes two or more surface ECG electrodes allowing for sensing of ECG signals. In a specific embodiment, monitoring electrode set 450 allows for sensing the standard 12-lead ECG.

Pacing electrode set 230, defibrillation electrode set 448, and monitoring electrode set 450 are each selected from body-surface electrodes 405. In various embodiments, each electrode of body-surface electrodes 405 is selectable for being an electrode of one, two, or all of pacing electrode set 230, defibrillation electrode set 448, and monitoring electrode set 450. In various embodiments, two or all of pacing electrode set 230, defibrillation electrode set 448, and monitoring electrode set 450 share one or more common electrodes.

In the illustrated embodiment, accelerometer 452 is shown as part of body-surface electrodes 405 because it is incorporated into an adhesive pad electrode. In various embodiments, accelerometer 452 is incorporated into an electrode of one of pacing electrode set 230, defibrillation electrode set 448, and monitoring electrode set 450. Accelerometer 452 senses an acceleration signal indicative of skeletal muscle contractions resulting from the pacing pulses delivered through pacing electrode set 230.

Cable 410 provides for the electrical connections between transcutaneous cardiac stimulation device 420 and body-surface electrodes 405. An example of cable 410 is illustrated as cable 110 in FIG. 1. In various embodiments, cable 410 represents any form of electrical conductors connecting between electrode interface 446 and body-surface electrodes 405.

Figure 5:
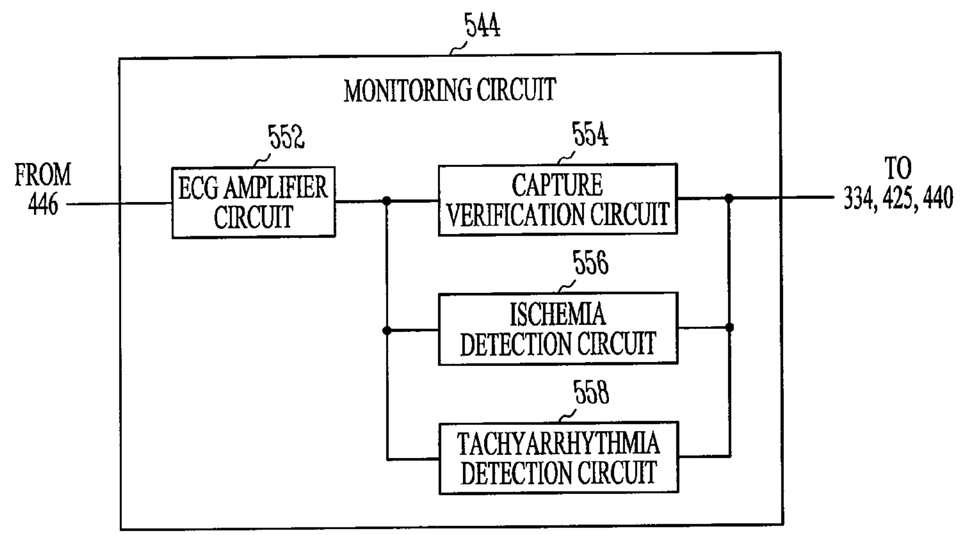
FIG. 5 is a block diagram illustrating an embodiment of a monitoring circuit of the transcutaneous cardiac stimulation device.

FIG. 5 is a block diagram illustrating an embodiment of a monitoring circuit 544, which is an embodiment of monitoring circuit 444. Monitoring circuit 544 includes an ECG amplifier circuit 552, a capture verification circuit 554, an ischemia detection circuit 556, and a tachyarrhythmia detection circuit 558. ECG amplifier circuit 552 senses one or more ECG signals through monitoring electrode set 450 and processes the one or more ECG signals. In one embodiment, ECG amplifier circuit 552 senses and processes the standard 12-lead ECG.

Capture verification circuit 554 determines whether each pacing pulse delivered through pacing electrode set 230 results in a cardiac depolarization using the one or more ECG signals. In one embodiment, capture verification circuit 554 further determines a capture percentage associated with pacing electrode set 230 and one or more specified pacing energy parameters including pacing amplitude and/or pulse width. The capture percentage is a percentage of the pacing pulses resulting in cardiac depolarizations. Capture verification circuit 554 produces a capture verification signal indicative of the capture percentage.

Ischemia detection circuit 556 detects an ischemia event using the one or more ECG signals and produces an ischemia signal indicative of a detection of the ischemia event. In one embodiment, ischemia detection circuit 556 locates an ischemic region in heart 101 using ECG signals sensed through multiple electrode pairs of monitoring electrode set 450, and produces an ischemia signal indicative of an approximate location of the ischemic region. It allows selection of pacing electrode set 230 from body-surface electrodes 405 for directing the pacing pulses to ischemic or non-ischemic regions of heart 101, depending on the purpose of pacing.

Tachyarrhythmia detection circuit 558 detects one or more specified types of tachyarrhythmia indicated for defibrillation therapy using the one or more ECG signals and produces a tachyarrhythmia detection signal indicative of a detection of a specified type tachyarrhythmia. In one embodiment, defibrillation control circuit 440 initiates the delivery of a defibrillation pulse in response to the tachyarrhythmia detection signal. This allows timely treatment of tachyarrhythmia that occurs during the delivery of the pacing cardioprotection therapy.

Figure 6:
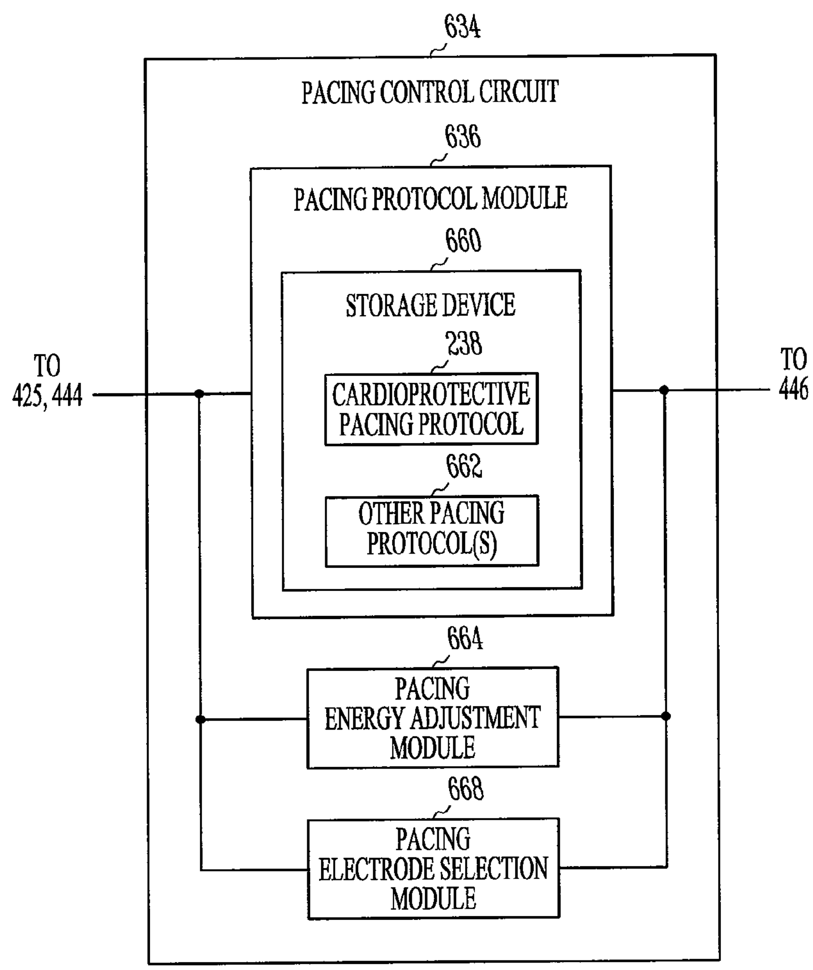
FIG. 6 is a block diagram illustrating an embodiment of a pacing control circuit of the transcutaneous cardiac stimulation device.

FIG. 6 is a block diagram illustrating an embodiment of a pacing control circuit 634, which is an embodiment of pacing control circuit 434. Pacing control circuit 634 includes a pacing protocol module 636, a pacing energy adjustment module 664, and a pacing electrode selection module 668. In one embodiment, pacing control circuit 634 starts executing a pacing protocol in response to a pacing command received from the user by user interface 425. In one embodiment, pacing control circuit 634 stops executing the pacing protocol in response to one of a pacing termination command received from the user by user interface 425 and the tachyarrhythmia detection signal produced by tachyarrhythmia detection circuit 558. The pacing protocol includes cardioprotective pacing protocol 238.

Pacing protocol module 636 includes a storage device 660 that stores at least cardioprotective pacing protocol 238. In the illustrated embodiment, storage device 660 also stores one or more other pacing protocols 662, such as an anti-arrhythmia pacing protocol specifying a pacing therapy to be delivered in coordination with the defibrillation therapy. In one embodiment, cardioprotective pacing protocol 238 is a patient-specific protocol customized for each individual patient, with pacing parameters selected and/or adjusted based on the patient's current conditions and cardiac history. Examples of such pacing parameters include the number of pacing cycles (each including a pacing period and a non-pacing period), the pacing period, the non-pacing period, the pacing energy parameter(s) including pacing amplitude and/or pulse width, and the pacing mode. In one embodiment, cardioprotective pacing protocol 238 is a disease-specific protocol customized for one or more cardiac and/or non-cardiac diseases. Certain diseases affect the effectiveness of the pacing cardioprotection therapy and hence require higher dosage of the pacing cardioprotection therapy. For example, higher pacing energy is likely required for producing the cardioprotective effect when the patient is diabetic.

Pacing energy adjustment module 664 determines the pacing energy parameters associated with pacing electrode set 230. The pacing energy parameters include pacing amplitude and pulse width. At least one of the pacing amplitude and pulse width is adjustable. In one embodiment, the pacing pulses are of constant-current-type with the pacing amplitude adjustable in a range between approximately 10 to 140 milliamperes, and the pacing pulse width adjustable in a range between approximately 2 to 100 milliseconds. In one embodiment, pacing energy adjustment module 664 adjusts one or more of the pacing energy parameters by comparing the capture percentage to a capture threshold. The capture threshold is specified to a satisfactory or acceptable value, such as 80%. Pacing energy adjustment module 664 increases pacing energy if the capture percentage is below the specified capture threshold. In one embodiment, pacing energy adjustment module 664 receives a skeletal muscular stimulation signal indicative of a level of the patient's skeletal muscular contractions resulting from the pacing pulses, and adjusts the pacing energy using the capture percentage and the skeletal muscular stimulation signal. In one embodiment, the skeletal muscular stimulation signal is the acceleration signal sensed by accelerometer 452. Pacing energy adjustment module 664 decreases the pacing energy if the acceleration signal is above a specified stimulation threshold while the capture percentage exceeds the specified capture threshold. In other embodiments, the skeletal muscular stimulation signal includes any signal indicative of the level of the skeletal muscular contractions, such as a displacement signal indicative of muscular movements or a biopotential signal indicative of myoelectric activities. In one embodiment, pacing energy adjustment module 664 adjusts the pacing energy dynamically during the execution of cardioprotective pacing protocol 238. In one embodiment, pacing energy adjustment module 664 adjusts one or more of the pacing energy parameters when the capture percentage is below the specified capture threshold. In another embodiment, pacing energy adjustment module 664 adjusts one or more of the pacing energy parameters to maintain the capture percentage at about the specified capture threshold. In various embodiments, pacing energy adjustment module 664 dynamically adjusts one or more of the pacing energy parameters during the execution of the cardioprotective pacing protocol to ensure effectiveness of the pacing cardioprotection therapy.

Pacing electrode selection module 668 adjusts the selection of pacing electrode set 230 from body-surface electrodes 405 using one or more of the capture percentage, the pacing energy parameters, and the ischemia signal. For example, when the capture percentage falls below the specified capture threshold while the pacing energy cannot be increased, such as when the maximum energy capability of pacing output circuit 232 is reached or when the acceleration signal indicates an unacceptable level of skeletal muscular stimulation resulting from the pacing pulses, pacing electrode selection module 668 selects a different pacing electrode set 230 from body-surface electrodes 405. In another example, pacing electrode selection module 668 selects pacing electrode set 230 from body-surface electrodes 405 to avoid directing the pacing pulses to the ischemic region using the ischemia signal.

Figure 7:
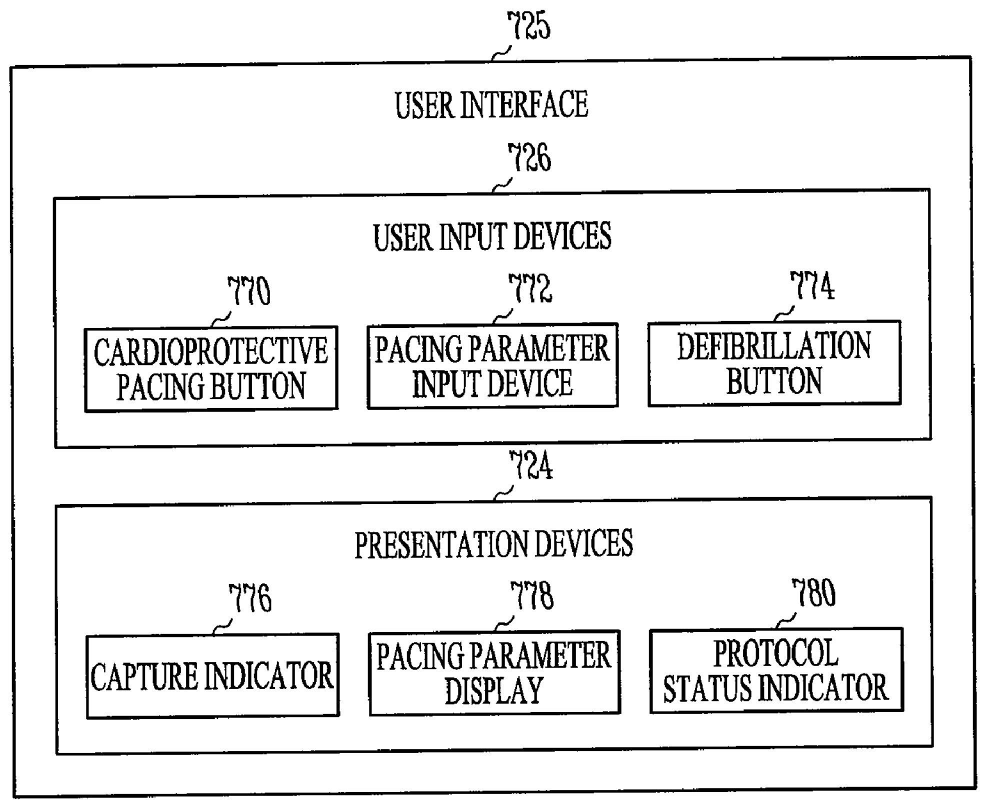
FIG. 7 is a block diagram illustrating an embodiment of a user interface of the transcutaneous cardiac stimulation device.

FIG. 7 is a block diagram illustrating an embodiment of a user interface 725, which is an embodiment of user interface 425. User interface 725 includes user input devices 726 and presentation devices 724.

User input devices 726 include a cardioprotective pacing button 770, a pacing parameter input device 772, and a defibrillation button 774. Cardioprotective pacing button 770 receives the cardioprotective pacing command from the user to start an execution of the cardioprotective pacing protocol. Pacing parameter input device 772 allows adjustment of one or more programmable pacing parameters. In one embodiment, pacing parameter input device 772 allows the user to overwrite parameter values specified in the stored cardioprotective pacing protocol and/or the parameter values produced by pacing energy adjustment module 664. Defibrillation button 774 receives the defibrillation command that initiates the delivery of a defibrillation pulse. The defibrillation command also stops the execution of the cardioprotective pacing protocol. In various embodiments, user input devices 726 includes devices to receive other user commands, such as the pacing termination command that stops the execution of the cardioprotective pacing protocol. In various embodiments, functions of cardioprotective pacing button 770, pacing parameter input device 772, and defibrillation button 774 are performed by user input devices in any configurations that are capable of receiving commands from the user, such as push buttons, keypad, dials, and interactive screen.

Presentation devices 724 include a capture indicator 776, a pacing parameter display 778, and a protocol status indicator 780. Capture indicator 776 indicate whether each pacing pulse delivered through pacing electrode set 230 captures the heart. In one embodiment, capture indicator 776 indicates the capture percentage. Pacing parameter display 778 presents values of selected pacing parameters, including the parameters that are adjustable using pacing parameter input device 772. Protocol status indicator 780 indicates one or more of whether the cardioprotective pacing protocol is being executed, whether the pacing pulses are being delivered, and the percentage of the cardioprotective pacing sequence that has been completed. In various embodiments, functions of capture indicator 776, pacing parameter display 778, and protocol status indicator 780 are performed by presentation devices in any configurations that are visible or otherwise perceivable by the user, such as a display screen and light-emitting diodes.

Figure 8:
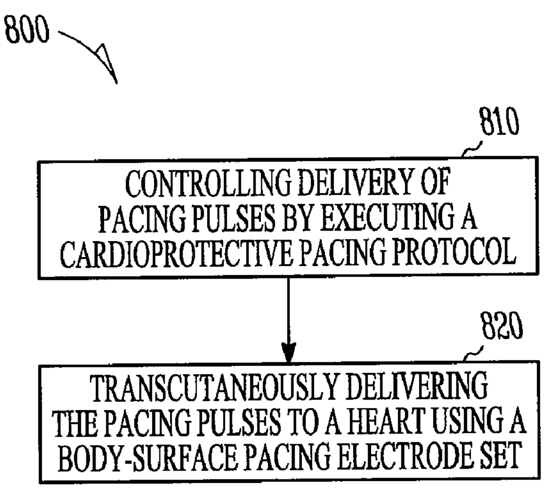
FIG. 8 is a flow chart illustrating an embodiment of a method for transcutaneously delivering cardioprotective pacing.

FIG. 8 is a flow chart illustrating of an embodiment of a method 800 for transcutaneously delivering cardioprotective pacing. In one embodiment, method 800 is performed by transcutaneous cardiac stimulation system 100, including its various embodiments discussed above with reference to FIGS. 1-7.

At 810, delivery of pacing pulses is controlled by executing a cardioprotective pacing protocol. The cardioprotective pacing protocol specifies a cardioprotective pacing sequence following which pacing pulses are delivered to augment mechanical stress on the myocardium of a patient's heart to a level effecting cardioprotection against myocardial injury. An example of the cardioprotective pacing protocol is discussed with reference to FIG. 3. At 820, the pacing pulses are delivered to the patient's heart from an external pacemaker through a pacing electrode set. The pacing electrode set includes at least two electrodes selected from a plurality of body-surface electrodes. The body-surface electrodes are configured to be attached onto the patient's skin and electrically wired to the external pacemaker.

Figure 9:
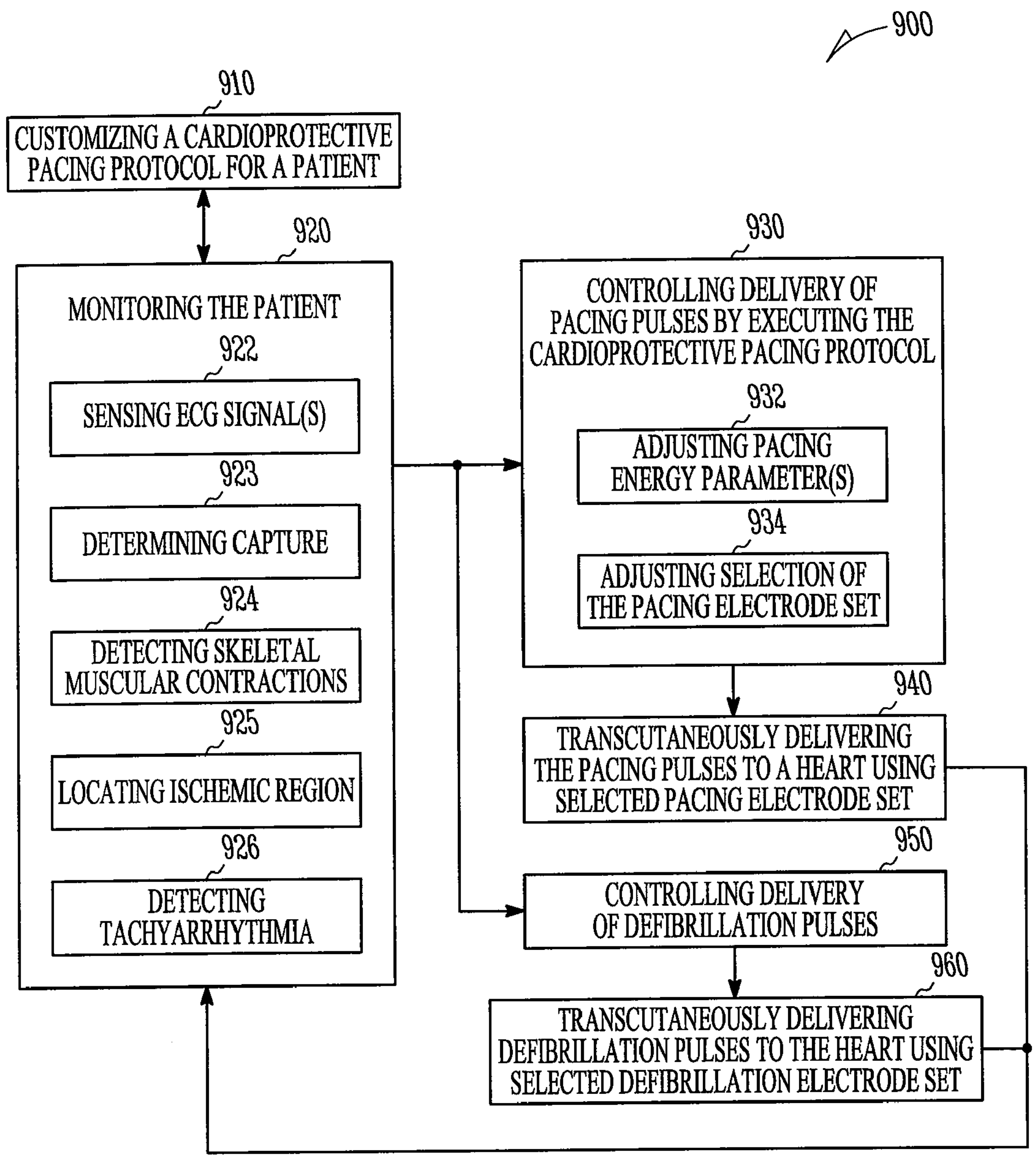
FIG. 9 is a flow chart illustrating another embodiment of the method for transcutaneously delivering cardioprotective pacing.

FIG. 9 is a flow chart illustrating of an embodiment of a method 900 for transcutaneously delivering cardioprotective pacing, which is another embodiment of method 800. In one embodiment, method 900 is performed by transcutaneous cardiac stimulation system 400, including the various embodiments of its components discussed above with reference to FIGS. 4-7.

At 910, the cardioprotective pacing protocol is customized for a patient. In one embodiment, the customization of the cardioprotective pacing protocol for the patient includes determination of values of one or more parameters based on the patient's medical history and examination results. Examples of such parameters include the number of pacing cycles (each including a pacing period and a non-pacing period), the pacing period, the non-pacing period, the pacing energy parameters such as the amplitude and pulse width, and pacing mode. These parameters determine the therapy dose, energy of each pacing pulse, and level of stress applied to the myocardium.

At 920, the patient is monitored in preparation to and during the execution of the cardioprotective pacing protocol. In the illustrated embodiment, the patient monitoring includes sensing one or more ECG signals at 922, determining capture at 923, detecting skeletal muscular contractions at 924, locating ischemic region at 925, and detecting tachyarrhythmia at 926. In one embodiment, the standard 12-lead ECG is sensed at 922. In another embodiment, one or more ECG signals required for controlling the pacing according to the cardioprotective pacing protocol are sensed at 922. Capture is verified at 923 by determining whether each delivered pacing pulse results in a cardiac depolarization. In one embodiment, a capture percentage is determined at 923. The capture percentage is the percentage of the pacing pulses resulting in cardiac depolarization and is associated with the pacing electrodes and the pacing energy parameters used. A capture verification signal indicative of the capture percentage is produced for the selected pacing electrode set and the specified pacing energy parameters. At 924, skeletal muscular contractions caused by the pacing pulses are detected by sensing a skeletal muscular stimulation signal indicative of skeletal muscle contractions resulting from the pacing pulses. In one embodiment, an accelerometer senses an acceleration signal as the skeletal muscular stimulation signal. The capture percentage and the acceleration signal allow for adjustment of pacing energy to obtain the intended therapeutic effect of pacing while minimizing the patient's discomfort caused by the pacing-induced skeletal muscle contractions. At 925, an ischemic region in the heart is approximately located using multiple ECG signals. This allows for directing the pacing pulses to target on, or to avoid targeting on the ischemic region. At 926, tachyarrhythmia of one or more specified types is detected. The specified types are those requiring defibrillation therapy. The detection of the specified type tachyarrhythmia indicates a need to defibrillate the patient and/or a need to terminate or suspend the delivery of pacing pulses.

At 930, the delivery of the pacing pulses is controlled by executing the cardioprotective pacing protocol. The execution is started in response to a pacing command received from a user. In one embodiment, the execution is stopped in response to a pacing termination command received from the user, or in response to a detection of the specified type tachyarrhythmia. Control of the delivery of the pacing pulses includes adjusting one or more of the pacing energy parameters at 932 and adjusting selection of the pacing electrode set at 934. One or both of the pacing amplitude and pacing pulse width are adjustable for controlling the pacing energy. The pacing electrode set is adjusted by selecting two or more electrodes from the plurality of available body-surface electrodes. In one embodiment, the parameter adjustment and/or electrode selection are performed manually by user. In another embodiment, the parameter adjustment and/or electrode selection are performed automatically by a device, such as transcutaneous cardiac stimulation device 420. In one embodiment, the parameter adjustment and/or electrode selection are performed before the execution of the cardioprotective pacing protocol. In another embodiment, one or more of the pacing energy parameters are dynamically adjustable during the execution of the cardioprotective pacing protocol. In another embodiment, the selection of the pacing electrode set is also dynamically adjustable during the execution of the cardioprotective pacing protocol. At 932, one or more of the pacing energy parameters are adjusted based on the detected capture percentage and the level of skeletal muscular contractions. In one embodiment, one or more of the pacing energy parameters are adjusted to maintain the pacing energy at approximately a specified capture threshold, such as about 80%, thereby securing the intended therapeutic effect of the cardioprotective pacing protocol while minimizing the patient's skeletal muscular stimulation. At 934, the selection of the pacing electrode set is adjusted using one or more of the capture percentage, the one or more pacing energy parameters, and the location of the ischemic region. For example, two more electrodes are selected from the plurality of available body-surface electrodes to ensure that the capture percentage can be maintained at about the specified capture threshold, to use the lowest possible pacing energy, and/or to target or avoid the ischemic region. At 940, the pacing pulses are transcutaneously delivered to the patient's heart using the selected pacing electrode set.

At 950, delivery of defibrillation pulses is controlled. In one embodiment, one or more defibrillation pulses are delivered in response to one of a defibrillation command received from the user and the detection of the specified type tachyarrhythmia. At 960, the one or more defibrillation pulses are transcutaneously delivered to the patient's heart using a defibrillation electrode set selected from the plurality of body-surface electrodes.

It is to be understood that the above detailed description is intended to be illustrative, and not restrictive. Other embodiments will be apparent to those of skill in the art upon reading and understanding the above description. The scope of the invention should, therefore, be determined with reference to the appended claims, along with the full scope of equivalents to which such claims are entitled.

What is claimed is:

1. A system for pacing a heart having a myocardium in a living body having a skin, the system comprising:
- a transcutaneous cardiac stimulation device including:
  - a pacing output circuit configured to produce pacing pulses suitable for capturing the heart by transcutaneous delivery; and
  - a pacing control circuit coupled to the pacing output circuit and configured to control the transcutaneous delivery of the pacing pulses by executing a pacing protocol, the pacing control circuit including a pacing protocol module and the pacing protocol stored in the pacing protocol module, the pacing protocol including a cardioprotective pacing protocol specifying a pacing mode adapted to augment mechanical stress on the myocardium to a level effecting cardioprotection against myocardial injury using the pacing pulses; and
- a plurality of body-surface electrodes including a pacing electrode set electrically wired to the pacing output circuit, the body-surface electrodes configured to be attached onto the skin, the pacing electrode set including at least two electrodes through which the pacing pulses are transcutaneously delivered to the heart.

2. The system of claim 1, wherein the transcutaneous cardiac stimulation device comprises a monitoring circuit including an electrocardiogram (ECG) amplifier circuit configured to sense one or more ECG signals using electrodes selected from the plurality of body-surface electrodes.

3. The system of claim 2, wherein the monitoring circuit comprises a capture verification circuit configured to determine whether each of the pacing pulses results in a cardiac depolarization.

4. The system of claim 3, wherein the capture verification circuit is configured to determine a capture percentage associated with specified values of pacing energy parameters and produce a capture verification signal indicative of the capture percentage, the capture percentage being a percentage of the pacing pulses resulting in cardiac depolarizations.

5. The system of claim 4, wherein the pacing control circuit comprises a pacing energy adjustment module configured to adjust the pacing energy parameters using the capture verification signal.

6. The system of claim 5, wherein the pacing control circuit comprises an electrode selection module configured to select the pacing electrode set from the plurality of body-surface electrodes and adjust the selection of the pacing electrode set using the capture verification signal and the pacing energy parameters.

7. The system of claim 5, wherein the pacing energy adjustment module is configured to receive a skeletal muscular stimulation signal indicative of a level of skeletal muscular contractions resulting from the pacing pulses delivered through the pacing electrode set and adjust the pacing energy parameters using the capture verification signal and the skeletal muscular stimulation signal.

8. The system of claim 7, comprising an accelerometer configured to sense an acceleration signal indicative of the level of the skeletal muscle contractions resulting from the pacing pulses delivered through the pacing electrode set, and wherein the pacing energy adjustment module is configured to adjust the pacing energy parameters using the capture verification signal and the acceleration signal.

9. The system of claim 8, wherein the accelerometer is incorporated into one of the body-surface electrodes.

10. The system of claim 9, wherein the body-surface electrodes each comprise an adhesive pad.

11. The system of claim 2, wherein the monitoring circuit comprises an ischemia detection circuit configured to detect an ischemia event using the one or more ECG signals and produce an ischemia signal indicative of a detection of the ischemia event, and the pacing control circuit is configured to control the delivery of the pacing pulses using the ischemia signal.

12. The system of claim 1, wherein the pacing control circuit is configured to start executing the cardioprotective pacing protocol in response to a cardioprotective pacing command, and the transcutaneous cardiac stimulation device comprises a user interface including a cardioprotective pacing button configured to receive the cardioprotective pacing command.

13. The system of claim 12, comprising:

a defibrillation output circuit configured to deliver defibrillation pulses suitable for defibrillating the heart by transcutaneous delivery through a defibrillation electrode set including at least two electrodes selected from the plurality of body-surface electrodes; and a defibrillation control circuit configured to control the delivery of the defibrillation pulses in response to a defibrillation command, and wherein the user interface comprises a defibrillation button configured to receive the defibrillation command.

14. The system of claim 13, comprising a tachyarrhythmia detection circuit configured to detect a specified type tachyarrhythmia and generate a tachyarrhythmia detection signal indicative of a detection of the specified type tachyarrhythmia, and wherein the defibrillation control circuit is configured to control the delivery of the defibrillation pulses in response to one of the defibrillation command and the tachyarrhythmia detection signal, and the pacing control circuit is configured to stop executing the pacing protocol in response to the one of the defibrillation command and the tachyarrhythmia detection signal.

15. A method for pacing a heart having a myocardium in a body, the method comprising:

delivering pacing pulses transcutaneously to the heart through a pacing electrode set including two or more electrodes selected from a plurality of body-surface electrodes configured to be attached onto the body;

controlling the delivery of the pacing pulses by executing a cardioprotective pacing protocol specifying a pacing mode adapted to augment mechanical stress on the myocardium to a level effecting cardioprotection against myocardial injury using the pacing pulses.

16. The method of claim 15, comprising:

sensing one or more electrocardiogram (ECG) signals; and determining whether each of the pacing pulses delivered through the pacing electrode set results in a cardiac depolarization using the one or more ECG signals.

17. The method of claim 16, comprising determining a capture percentage associated with the pacing electrode set and specified values of pacing energy parameters, the capture percentage being a percentage of the pacing pulses resulting in cardiac depolarizations in the heart, wherein controlling the delivery of the pacing pulses comprises controlling the delivery of the pacing pulses using the capture percentage.

18. The method of claim 17, comprising receiving a muscular stimulation signal indicative of skeletal muscular contractions resulting from the pacing pulses, and wherein controlling the delivery of the pacing pulses comprises adjust pacing energy parameters using the capture percentage and the muscular stimulation signal.

19. The method of claim 18, comprising adjusting the selection of the pacing electrode set from the plurality of body-surface electrodes using the capture percentage, the pacing energy parameters, and the muscular stimulation signal.

20. The method of claim 19, comprising:

locating an ischemic region in the heart; and producing an ischemia signal indicative of an approximate location of the ischemic region, and wherein controlling the delivery of the pacing pulses comprises controlling the delivery of the pacing pulses using the capture percentage and the ischemia signal.

21. The method of claim 20, comprising selecting the pacing electrode set from the plurality of body-surface electrodes using the ischemic signal.

22. The method of claim 16, comprising:

detecting a specified type tachyarrhythmia using the one or more ECG signals;

stopping the execution of the cardioprotective pacing protocol in response to a detection of the specified type tachyarrhythmia; and delivering a defibrillation pulse to the heart using a defibrillation electrode set including at least two defibrillation electrodes selected from the plurality of body-surface electrodes in response to the detection of the specified type tachyarrhythmia.

23. The method of claim 15, comprising customizing the cardioprotective pacing protocol for each individual patient.

24. The method of claim 23, wherein the cardioprotective pacing protocol specifies a cardiac protection pacing sequence including a specified number of cycles of alternating pacing and non-pacing periods, the pacing periods each specified as a pacing duration during which pacing pulses are delivered using one or more specified pacing energy parameters including one or more of a pacing amplitude and a pacing pulse width, the non-pacing periods each specified as a non-pacing duration during which no pacing pulse is delivered, and customizing the cardioprotective pacing protocol comprises determining values of one or more of the specified number of cycles of alternating pacing and non-pacing periods, the specified pacing period, the specified non-pacing period, and the one or more specified pacing energy parameters.

* * * * *